(12) United States Patent
Hardy et al.

(10) Patent No.: US 8,143,420 B2
(45) Date of Patent: Mar. 27, 2012

(54) BIFUNCTIONAL AND TRIFUNCTIONAL NITRONE SPIN TRAPPING COMPOUNDS AND USES THEREOF

(75) Inventors: Micael Joel Hardy, La Seyne sur mer (FR); Marcos Lopez, Wauwatosa, WI (US); Balaraman Kalyanaraman, Wauwatosa, WI (US); Neil Hogg, New Berlin, WI (US); Olivier Ouari, Seynod (FR); Paul Tordo, Marsielle (FR)

(73) Assignees: Medical Collage of Wisconsin, Inc., Milwaukee, WI (US); Université de Provence, Marsielle (FR)

( * ) Notice: Subject to any disclaimer, the term of this patent is extended or adjusted under 35 U.S.C. 154(b) by 446 days.

(21) Appl. No.: 12/343,975

(22) Filed: Dec. 24, 2008

(65) Prior Publication Data

US 2009/0170134 A1 Jul. 2, 2009

Related U.S. Application Data

(60) Provisional application No. 61/018,148, filed on Dec. 31, 2007.

(51) Int. Cl.
*C07D 403/00* (2006.01)
(52) U.S. Cl. .................................................. 548/302.7
(58) Field of Classification Search ................ 548/302.7
See application file for complete search history.

(56) References Cited

U.S. PATENT DOCUMENTS 5,354,871 A * 10/1994 Arya et al. ..................... 548/542
7,589,210 B2 * 9/2009 Tordo et al. ................... 548/111

FOREIGN PATENT DOCUMENTS

WO WO2005/081622 A1 2/2005

OTHER PUBLICATIONS

Chalier et al., Journal of Organic Chemistry, 2007, 72: 7886-7892.*
Arya et al. CAS: 121:255629, 1994.*
Adlam V, et al., "Targeting an antioxidant to mitochondria decreases cardiac ischemia-reperfusion injury." FASEB J. 19:1088-1095 (2005).
Blaikie F, et al., "Targeting dinitrophenol to mitochondria: limitations to the development of a self-limiting mitochondrial protonophore." Biosci. Rep. 26:231-243 (2006).
Chalier F, et al., "ESR study of spin-trapping with two glycosylated analogues of PBN able to target cell membrane lectins." Org. Biomol. Chem. 2:927-934 (2004).
Chen L & Harrison S, "Cell-penetrating peptides in drug development: enabling intracellular targets." Biochem. Soc. Trans. 35:821-825 (2007).
Fawell S, et al., "Tat-mediated delivery of heterologous proteins into cells." Proc. Natl. Acad. Sci. USA 91:664-668 (1994).
Filipovska A, et al., "Synthesis and characterization of a triphenylphosphoniumconjugated peroxidase mimetic." J. Biol. Chem. 280:24113-24126 (2005).
Frejaville C, et al., "5-Diethoxyphosphoryl-5-methyl-1-pyrroline N-oxide (DEPMPO): a new phosphorylated nitrone for the efficient in vitro and in vivo spin trapping of oxygen-centred radicals." J. Chem. Soc., Chem. Commun. 1793-1794 (1994).
Frejaville C, et al., "5-(Diethoxyphosphoryl)-5-methyl-1-pyrroline N-oxide: a New efficient phosphorylated nitrone for the in vitro and in vivo spin trapping of oxygen-centered radicals." J. Med. Chem. 38:258-265 (1995).
Hardy M, et al., "Mito-DEPMPO synthesized from a novel NH2-reactive DEPMPO spin trap: a new and improved trap for the detection of superoxide." Chem. Commun. (Camb) 10:1083-1085 (2007).
Hay A, et al., Development of new EPR spin trap, DOD-8C (N-[4-dodecyloxy-2-(7'-carboxyhept-1'-yloxy)benzylidene]-N-tert-butylamine N-oxide), for the trapping of lipid radicals at a predetermined depth within biological membranes Arch. Biochem. Biophys. 435:336-346 (2005).
Jaffrey S, et al.,"Protein S-nitrosylation: a physiological signal for neuronal nitric oxide." Nat. Cell Biol. 3:193-197 (2001).
James A, et al., "Interactions of Mitochondria-targeted and Untargeted Ubiquinones with the Mitochondrial Respiratory Chain and Reactive Oxygen Species." J. Biol. Chem. 280,:21295-21312 (2005).
Janzen E & Blackburn B, "Detection and identification of short-lived free radicals by an electron spin resonance trapping technique." J. Am. Chem. Soc. 90:5909-5910 (1968).
Katsumi H, et al., "Physicochemical, tissue distribution, and vasodilation characteristics of nitrosated serum albumin: delivery of nitric oxide in vivo." J. Pharm. Sci. 93:2343-2352 (2004).
Kelman D, et al., "Reaction of myoglobin with hydrogen peroxide forms a peroxyl radical which oxidizes substrates." J. Biol. Chem. 269:7458-7463 (1994).
Kettenhofen N, et al., "Proteomic methods for analysis of S-nitrosation." J. Chromatogr. B Analyt. Technol. Biomed. Life Sci. 851:152-159 (2007).
Knutson K, et al., "T-cell immunity to the folate receptor alpha is prevalent in women with breast or ovarian cancer." J. Clin. Oncol. 24:4254-4261 (2006).
Leamon C, et al, "Synthesis and biological evaluation of EC140: a novel folate-targeted vinca alkaloid conjugate." Bioconjugate Chem. 17:1226-1232 (2006).
Leamon C, et al., "Synthesis and biological evaluation of EC72: a new folate-targeted chemotherapeutic." Bioconj. Chem. 16:803-811 (2005).
Liu Y, et al., "A novel spin trap for targeting sulfhydryl-containing polypeptides." Chem. Commun. (Camb) 39:4943-4945 (2005).
Lu Y, et al., "Preclinical pharmacokinetics, tissue distribution, and antitumor activity of a folate-hapten conjugate-targeted immunotherapy in hapten-immunized mice." Mol. Cancer Ther. 5:3258-3267 (2006).
Lu Y, et al., "Folate receptor-targeted immunotherapy of cancer: mechanism and therapeutic potential." Adv. Drug Deliv. Rev. 56:1161-1176 (2004).

(Continued)

Primary Examiner — Rei-tsang Shiao
(74) Attorney, Agent, or Firm — Quarles & Brady LLP; Sara D. Vinarov

(57) ABSTRACT

Methods and compositions for detecting free radicals, the compositions being spin trapping compounds comprising a nitrone having a detecting moiety and optionally having a targeting moiety for targeting the nitrone to an organ, a cell, an organelle or a molecule of interest for directly detecting free radicals, especially free radicals in biological samples.

13 Claims, 10 Drawing Sheets

OTHER PUBLICATIONS

Marshall N, et al., "Arginine-rich cell-penetrating peptides facilitate delivery of antisense oligomers into murine leukocytes and alter pre-mRNA splicing." J. Immunol. Methods 325:114-126 (2007).

Mason R, "Using anti-5,5-dimethyl-1-pyrroline N-oxide (anti-DMPO) to detect protein radicals in time and space with immuno-spin trapping." Free Radic. Biol. Med. 36:1214-1223 (2004).

McCusker C, et al., "Inhibition of experimental allergic airways disease by local application of a cell-penetrating dominant-negative STAT-6 peptide." J. Immunol. 179:2556-2564 (2007).

Moschos S, et al., "Cell-penetrating-peptide-mediated siRNA lung delivery." Biochem. Soc. Trans. 35:807-810 (2007).

Moulton H, et al., "Cell-penetrating peptide-morpholino conjugates alter pre-mRNA splicing of DMD (Duchenne muscular dystrophy) and inhibit murine coronavirus replication in vivo." Biochem. Soc. Trans. 35:826-828 (2007).

Murphy M & Smith R, "Targeting antioxidants to mitochondria by conjugation to lipophilic cations." Annu. Rev. Pharmacol. Toxicol. 47:629-656 (2007).

Murphy M, et al., "Superoxide activates uncoupling proteins by generating carbon-centered radicals and initiating lipid peroxidation." J. Biol. Chem. 278:48534-48545 (2003).

Olive G, et al., "2-ethoxycarbonyl-2-methyl-3,4-dihydro-2H-pyrrole-1-oxide: evaluation of the spin trapping properties." Free Rad. Biol. Med. 28:403-408 (2000).

Ouari O, et al., "Synthesis of a glycolipidic amphiphilic nitrone as a new spin trap." J. Org. Chem. 64:3554-3556 (1999).

Parker N, et al., "Folate receptor expression in carcinomas and normal tissues determined by a quantitative radioligand binding assay." Anal. Biochem. 338:284-293 (2005).

Reddy J, et al., "Preclinical evaluation of EC145, a folate-vinca alkaloid conjugate." Cancer Res. 67: 4434-4442 (2007).

Reddy J, et al., "Folate receptor specific anti-tumor activity of folate-mitomycin conjugates ." Cancer Chemother. Pharmacol. 58:229-236 (2006).

Ross M, et al., "Accumulation of lipophilic dications by mitochondria and cells ." Biochem. J. 400:199-208 (2006).

Samouilov A & Zweier J, "Development of chemiluminescence-based methods for specific quantitation of nitrosylated thiols." Anal. Biochem. 258:322-330 (1998).

Slofstra S, et al., "Protease-activated receptor-4 inhibition protects from multiorgan failure in a murine model of systemic inflammation." Blood 110:3176-3182 (2007).

Smith R, et al., "Delivery of bioactive molecules to mitochondria in vivo." Proc. Natl. Acad. Sci. USA. 100:5407-5412 (2003).

Tam J, "Synthetic peptide vaccine design: synthesis and properties of a high-density multiple antigenic peptide system." Proc. Natl. Acad, Sci. USA, 85:5409-5413 (1988).

Torchlin V, et al., "Tatp-mediated intracellular delivery of pharmaceutical nanocarriers." Biochem. Soc. Trans. 35:816-820 (2007).

Toshchakov V & Vogel S, "Cell-penetrating TIR BB loop decoy peptides." Expert Opin. Biol. Ther. 7:1035-1050 (2007).

Vlahov I, et al., "An assembly concept for the consecutive introduction of unsymmetrical disulfide bonds: synthesis of a releasable multidrug conjugate of folic acid." J. Org. Chem. 72:5968-5972 (2007).

Vlahov I, et al., "Design and regioselective synthesis of a new generation of targeted chemotherapeutics. Part 1: EC145, a folic acid conjugate of desacetylvinblastine monohydrazide." Bioorg. Med. Chem. Lett. 16:5093-5096 (2006).

Weiss H, et al., "ADME investigations of unnatural peptides: distribution of a 14C-labeled beta 3-octaarginine in rats." Chem Biodivers. 4:1413-1437 (2007).

Wu R, et al., "Cell-penetrating peptides as transporters for morpholino oligomers: effects of amino acid composition on intracellular delivery and cytotoxicity ." Nucleic Acids Res. 35:5182-5191 (2007).

Yang J, et al., "Characterization of the pH of Folate Receptor-Containing Endosomes and the Rate of Hydrolysis of Internalized Acid-Labile Folate-Drug Conjugates." J. Pharmacol. Exp. Ther. 321:462-468 (2007).

Yang J, et al., "Evaluation of disulfide reduction during receptor-mediated endocytosis by using FRET imaging." Proc. Natl. Acad. Sci. USA 103:13872-13877 (2006).

Zeghdaoui A, et al., "B-Phosphorylated-phenyl-N-tert-butylnitrone (PBN) analogues: a new series of spin traps for oxyl radicals" J. Chem. Soc. Perkin Trans. 2:2087-2089 (1995).

Zhang Y & Hogg N, "The mechanism of transmembrane S-nitrosothiol transport." Proc. Natl. Acad. Sci. USA 101:7891-7896 (2004).

Zhang Y & Hogg N, "Formation and stability of S-nitrosothiols in RAW 264.7 cells." Am. J. Physiol. Lung Cell Mol. Physiol. 287:L467-L474 (2004).

Chalier F, et al. "Design of new derivatives of nitrone DEPMPO functionalized at C-4 for further specific applications in superoxide radical detection." J. Org. Chem. 72, 7886-7892 (2007).

Hardy M, et al. "A new bifunctional DEPMPO based spin trap: expaning the spin trap role." Abstracts from the 2007 Electron Paramagnetic Resonance Meeting, p. 2. (2007).

Hardy M, et al. "A new bifunctional DEPMPO based spin trap: expaning the spin trap role." Poster presented at the 2007 Electron Paramagnetic Resonance Meeting (2007).

* cited by examiner

BIFUNCTIONAL AND TRIFUNCTIONAL NITRONE SPIN TRAPPING COMPOUNDS AND USES THEREOF

CROSS-REFERENCE TO RELATED APPLICATIONS

This application claims priority to and benefit of U.S. Provisional Patent Application Ser. No. 61/018,148 filed Dec. 31, 2007, which is hereby incorporated herein by reference in its entirety.

STATEMENT REGARDING FEDERALLY SPONSORED RESEARCH OR DEVELOPMENT

This invention was made with United States government support awarded by the following agency: NIH 5R01HL067244 and NIH 2R01GM055792. The United States government has certain rights in this invention.

BACKGROUND OF THE INVENTION

Free radicals mediate numerous physiological and patho-physiological processes including, but not limited to, aging, cancer, atherosclerosis, neurodegenerative diseases, cardio-vascular diseases and diabetes. Free radicals are atomic or molecular species with unpaired electrons or an otherwise open shell configuration. The unpaired electrons are usually highly reactive, so free radicals are likely to take part in numerous chemical reactions.

Analyzing free radicals in biological samples/systems, however, has traditionally been challenging because free radicals are highly reactive entities with very short lifetimes. One method for analyzing free radicals is spin trapping coupled with electron paramagnetic resonance (EPR). Janzen E & Blackburn B, J. Am. Chem. Soc. 90:5909-5910 (1968). Spin trapping is based on a specific reaction between spin traps and free radicals that forms a paramagnetic spin adduct, which is less reactive than the free radicals, and thus accumulates in higher concentrations. Because spin adducts are paramagnetic, their EPR spectra provide information on the trapped free radical. Unfortunately, bioreduction and/or biooxidation of spin adducts can occur in biological applications of spin trapping. In addition, free radicals are often compartmentalized in biological samples/systems, and therefore not easily accessible for analysis.

More recent spin trapping methods utilize nitrone compounds that react with a target free radical to form a persistent and distinguishable spin adduct that can be detected by EPR spectroscopy. See, e.g., Fréjaville C, et al., J. Chem. Soc., Chem. Commun. 1793-1794 (1994); Fréjaville C, et al., J. Med. Chem. 38:258-265 (1995); Olive G, et al., Free Rad. Biol. Med. 28:403-408 (2000); Ouari O, et al., J. Org. Chem. 64:3554-3556 (1999); and Zeghdaoui A, et al., J. Chem. Soc. Perkin Trans. 2:2087-2089 (1995). These methods, however, each present its own set of limitations, which commonly include short persistency of the spin adducts, slow spin trapping kinetics, complicated spectra because of a mixture of the spin adducts and anisotropy of the signal when proteins are trapped. Consequently, identification of the spin adducts can be difficult.

One application of spin traps is to analyze mechanisms of protein S-nitrosation, which is a common NO-dependent, post-translational modification involved in numerous signaling pathways. While it is relatively straight forward to measure the total level of protein S-nitrosation using reductive chemiluminescence techniques (Samouilov A & Zweier J, Anal. Biochem. 258:322-330 (1998); and Zhang Y & Hogg N, Am. J. Physiol. Lung Cell Mol. Physiol. 287:L467-L474 (2004)), its detection of specific proteins currently relies on an indirect technique that involves a specific reduction of a S-nitroso group by ascorbate, followed by labeling of a newly formed thiol with a biotin label (Jaffrey S, et al., Nat. Cell Biol. 3:193-197 (2001)) or a fluorescent probe (Kettenhofen N, et al., J. Chromatogr. B Analyt. Technol. Biomed. Life Sci. 851:152-159 (2007)) in so-called 'switch' assays.

The reaction between ascorbate and S-nitrosothiols in switch assays, however, is not kinetically facile, and often times much higher levels of ascorbate have been used in this assay than originally proposed. In addition, the reaction lacks specificity, as numerous low molecular weight disulfides and other proteins have been shown to be reduced at significant rates under high-ascorbate conditions, leading to false positives. Moreover, several extracellular proteins, including serum albumin, result in positive signals with the biotin switch assay, but not with the chemiluminescence switch assay.

In addition to protein S-nitrosation, spin traps are used to analyze other protein free radicals, as well as lipid and nucleic acid free radicals.

Hence, there is a need for spin trapping compounds that trap free radicals and form persistent, detectable spin adducts that can be directly assessed by a variety of known methods. In addition, there is a need for spin trapping compounds that not only trap free radicals, but also can be targeted to an organ, a cell, an organelle or a molecule of interest.

SUMMARY OF THE INVENTION

The invention relates generally to compositions and methods for detecting free radicals, and relates more particularly to spin trapping nitrones having a detecting moiety and/or a targeting moiety for directly detecting free radicals in biological samples.

One aspect of the invention is a spin trapping compound for analyzing free radicals comprising a nitrone, a linker attached at $R_1$ or $R_2$, and a detecting moiety attached to the linker, where the nitrone has the following structure:

(Formula 1)

In an exemplary embodiment of this aspect, the nitrone is N-tert-butyl-alpha-phenyl nitrone (PBN), alpha-(4-pyridyl 1-oxide)-N-tert butylnitrone or 2'-sulfonyl PBN. In a further exemplary embodiment of this aspect, the nitrone is N-tert-butyl-alpha-phenyl nitrone.

In another exemplary embodiment of this aspect, the linker is a hydrocarbon, a polyester, a polyethylene glycol, a carbohydrate, a fluorocarbon, a nucleic acid, a peptide, a polyamine, an amino acid or combinations thereof. The linker joins the detection moiety to the nitrone. As noted above, the linker may be attached to the nitrone at $R_1$ or $R_2$.

In another exemplary embodiment of this aspect, the detecting moiety is a small molecule, a chromogenic molecule, a fluorescent molecule or a radioactive molecule. In a further exemplary embodiment of this aspect, when the detecting molecule is a small molecule, it is biotin.

In another exemplary embodiment of this aspect, the spin trapping compound further comprises a targeting moiety linked to the nitrone. The targeting moiety may be linked either to the linker or may be linked directly to the nitrone at a R group not occupied by the linker and detecting moiety. The targeting moiety can be an organ targeting agent, a cell targeting agent, an organelle targeting agent or a molecule targeting agent. In a further exemplary embodiment, when the targeting moiety is a cell targeting agent, it is a folate, which targets specific folate receptors in cells. In a further exemplary embodiment of this aspect, when the targeting moiety is an organelle targeting agent, it is a mitochondrial targeting agent, such as a triphenylphosphonium cation, a pyridinium cation or a tetraalkyl ammonium cation. In a further exemplary embodiment of this aspect, when the targeting moiety is a molecule targeting agent, it is biotin.

A second aspect of the invention is a spin trapping compound for analyzing free radicals comprising a nitrone, a linker attached at $R_1$, $R_2$, $R_3$, $R_4$, $R_5$, $R_6$ or $R_7$, and a detecting moiety attached to the linker, where the nitrone has the following structure:

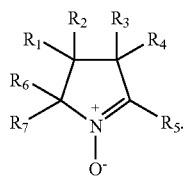

Formula 2)

In an exemplary embodiment of this aspect, the nitrone is 5-(diethoxy-phosphoryl)-5-methyl-1-pyrroline-N-oxide, 5-tert-butoxycarbonyl 5-methyl-1-pyrroline N-oxide, 5-(diisopropoxyphosphoryl)-5-methyl-1-pyrroline-N-oxide, 5-ethoxycarbonyl-5-methyl-1-pyrroline N-oxide, 5-carbamoyl-5-methyl-1-pyrroline N-oxide, 5,5-dimethyl-1-pyrroline 1-oxide, 5-(dipropoxyphosphoryl)-5-methyl-1-pyrroline N-oxide, 5-(di-n-butoxyphosphoryl)-5-methyl-1-pyrroline N-oxide or 5-(bis-(2-ethylhexyloxy)phosphoryl)-5-methyl-1-pyrroline N-oxide. In a further exemplary embodiment of this aspect, the nitrone is 5-(diethoxy-phosphoryl)-5-methyl-1-pyrroline-N-oxide.

In another exemplary embodiment of this aspect, the linker is a hydrocarbon, a polyester, a polyethylene glycol, a carbohydrate, a fluorocarbon, a nucleic acid, a peptide, a polyamine, an amino acid or combinations thereof. The linker joins the detection moiety to the nitrone. As noted above, the linker may be attached to the nitrone at $R_1$, $R_2$, $R_3$, $R_4$, $R_5$, $R_6$ or $R_7$.

In another exemplary embodiment of this aspect, the detecting moiety is a small molecule, a chromogenic molecule, a fluorescent molecule or a radioactive molecule. In a further exemplary embodiment of this aspect, when the detecting molecule is a small molecule, it is biotin.

In another exemplary embodiment of this aspect, the spin trapping compound further comprises a targeting moiety linked to the nitrone. The targeting moiety may be linked either to the linker or may be linked directly to the nitrone at a R group not occupied by the linker and detecting moiety. The targeting moiety can be an organ targeting agent, a cell targeting agent, an organelle targeting agent, or a molecule targeting agent. In a further exemplary embodiment, when the targeting moiety is a cell targeting agent, it is a folate, which targets specific folate receptors in cells. In a further exemplary embodiment of this aspect, when the targeting moiety is an organelle targeting agent, it is a mitochondrial targeting agent, such as a triphenylphosphonium cation, a pyridinium cation or a tetraalkyl ammonium cation. In a further exemplary embodiment of this aspect, when the targeting moiety is a molecule targeting agent, it is biotin.

A third aspect of the invention is a method of detecting free radicals, the method comprising the steps of reacting a sample suspected of having free radicals to a spin trapping compound as described above to form a spin adduct; optionally forming the free radicals by photolysis during the reacting step; and detecting the spin adduct.

In an exemplary embodiment of this aspect, the detecting moiety is detected via enzyme-linked immunosorbent assays, fluorescence microscopy, fluorescence spectroscopy, Northern blot analysis, Southern blot analysis, Western blot analysis, Immunodot assays, high performance liquid chromatography, mass spectrometry, magnetic resonance imaging, positron emission tomography or single photon emission computed tomography.

In another exemplary embodiment of this aspect, the spin adduct itself is detected via EPR.

It is an advantage that the compounds and methods described herein permit localized, targeted detection of free radicals in vitro and in vivo.

It is another advantage that the compounds and methods described herein permit the analysis of free radicals independent of the use of EPR.

It is another advantage that the compounds described herein broaden the application of spin trapping by combining spin trapping specificity with the sensitivity of methods for detecting certain detection moieties, such as an anti-biotin antibody.

These and other features, objects and advantages of the present invention will become better understood from the description that follows. In the description, reference is made to the accompanying drawings, which form a part hereof and in which there is shown by way of illustration, not limitation, embodiments of the invention. The description of exemplary embodiments or examples is not intended to limit the invention to cover all modifications, equivalents and alternatives. Reference should therefore be made to the claims recited herein for interpreting the scope of the invention.

BRIEF DESCRIPTION OF DRAWINGS OF EXEMPLARY EMBODIMENTS

Figure 1:
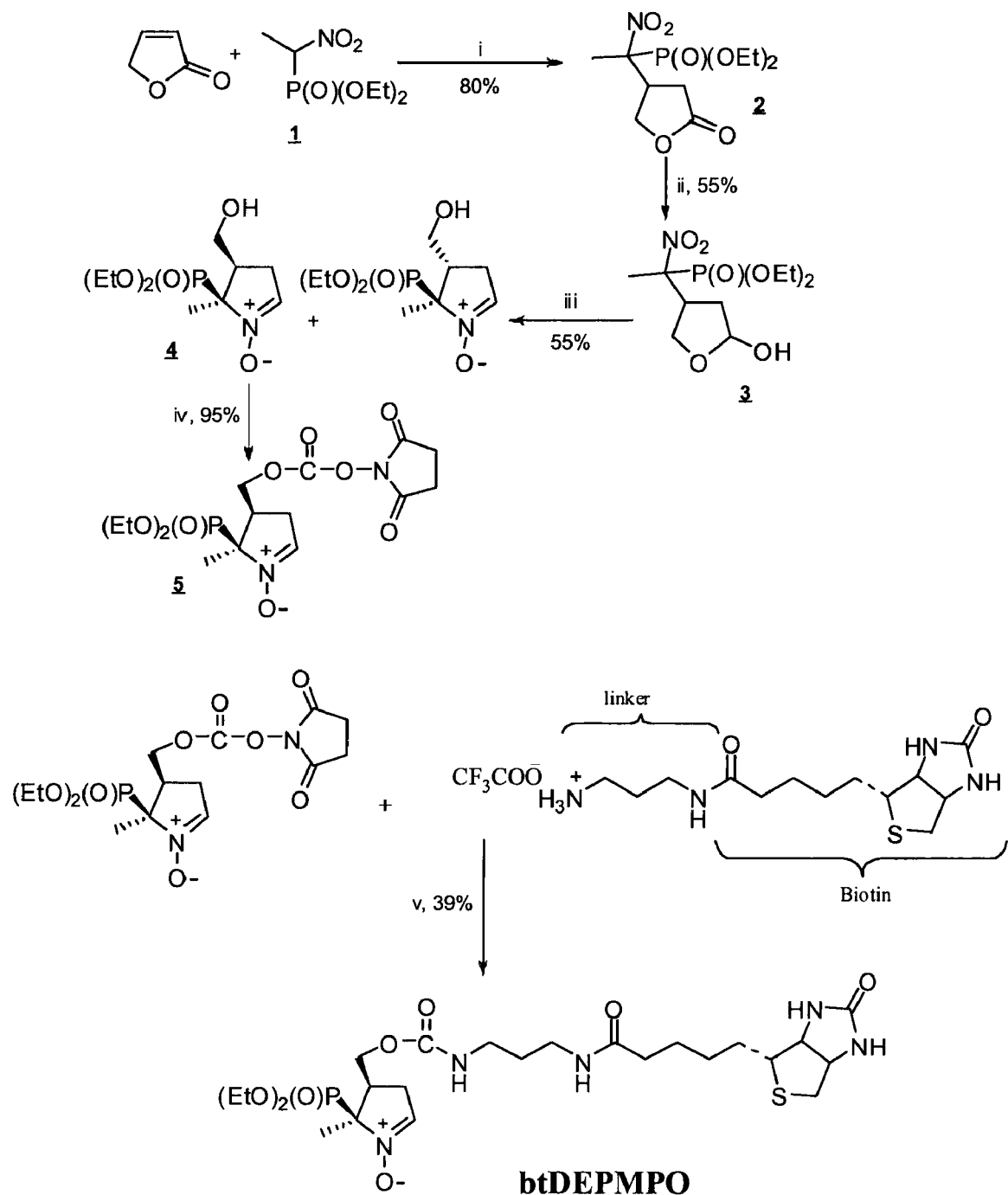
FIG. 1 shows a diagram for the synthesis of one embodiment of a bifunctional spin trapping compound, biotinylated DEPMPO (btDEPMPO)
Figure 2:
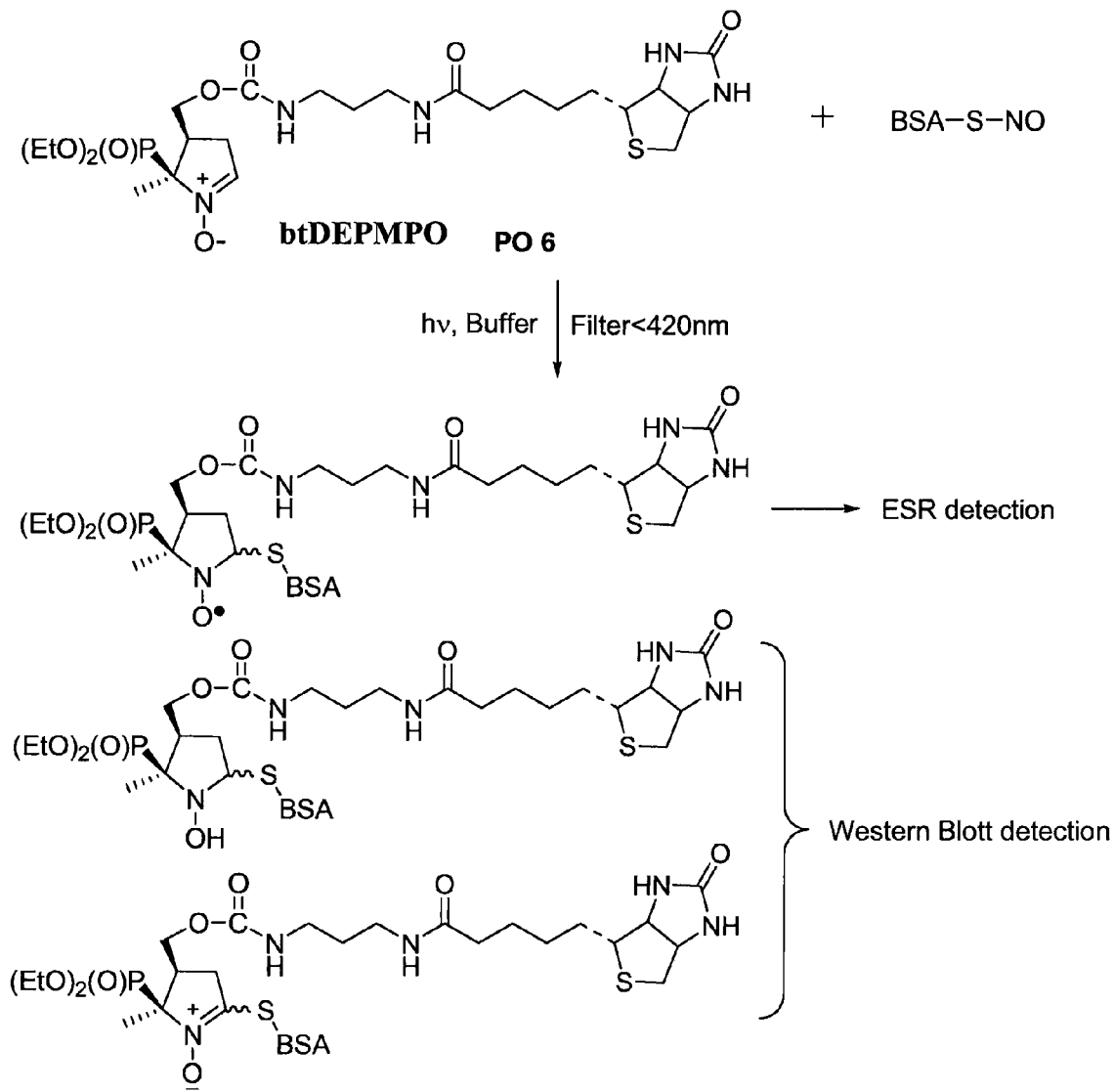
FIG. 2 shows a diagram for the use of btDEPMPO to detect free radicals, such as thiyl radicals generated after photolysis of protein S-nitrosothiols.
Figure 3:
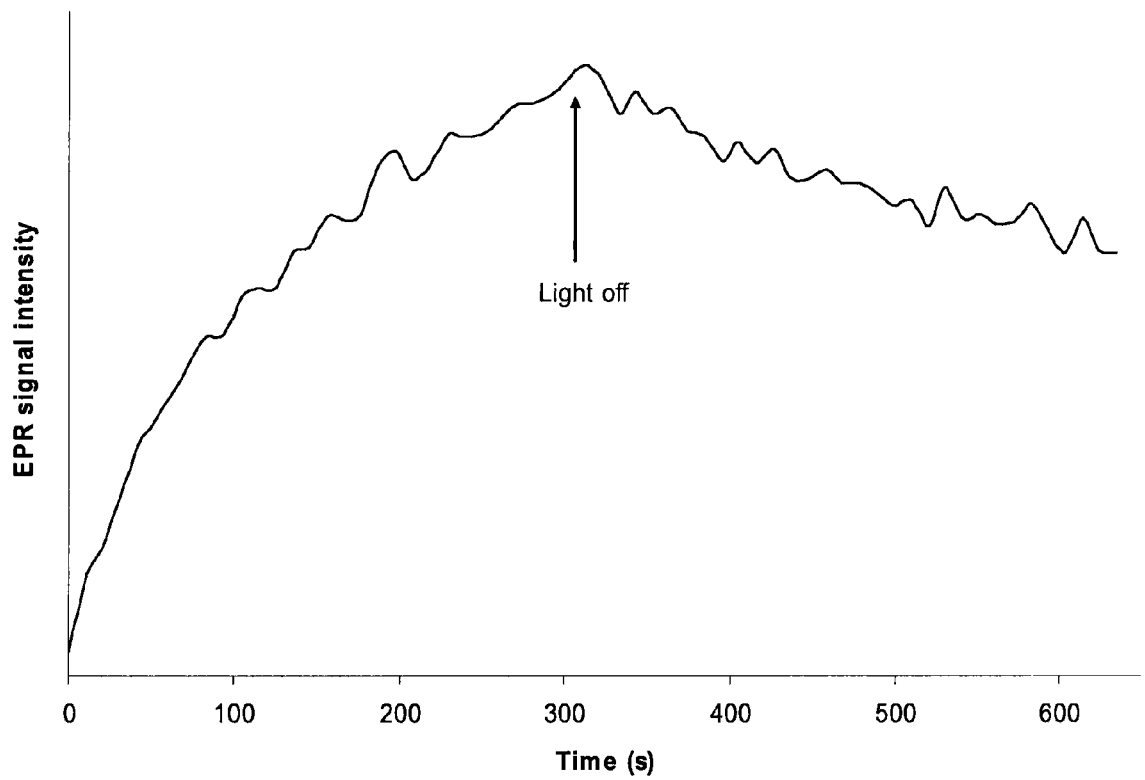
FIG. 3 shows a time course of a spectra recorded by EPR using singular value decomposition (SVD) analysis after photolysis of a solution containing S-nitrosated bovine serum albumin (BSA-SNO) and btDEPMPO.
Figure 4:
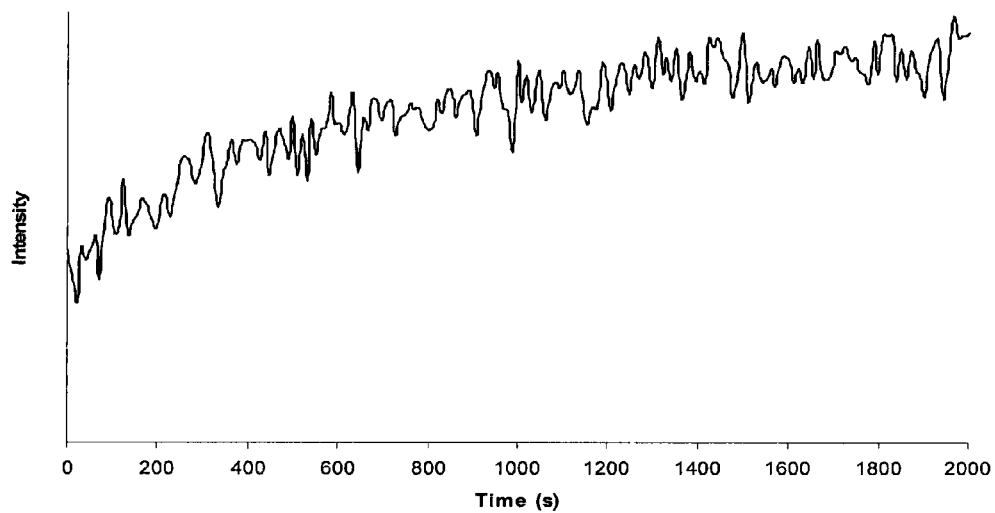
Figure 4:
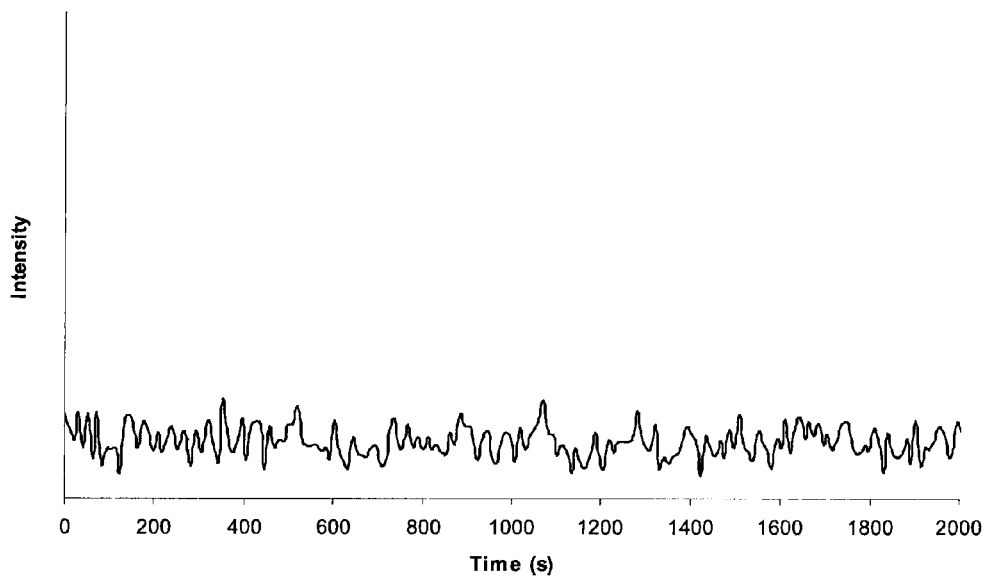
Figure 5:
Figure 6:
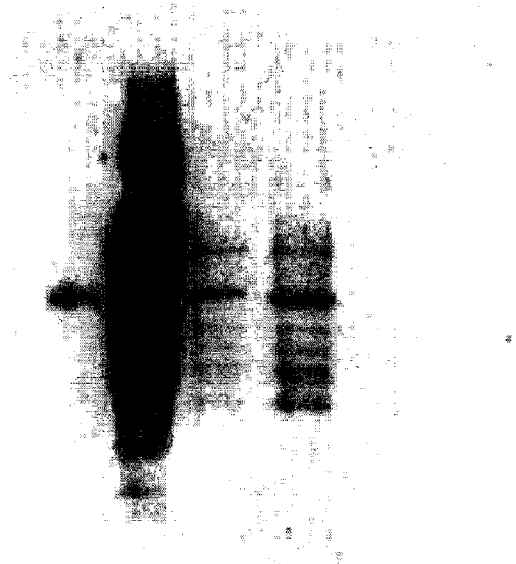
Figure 7:
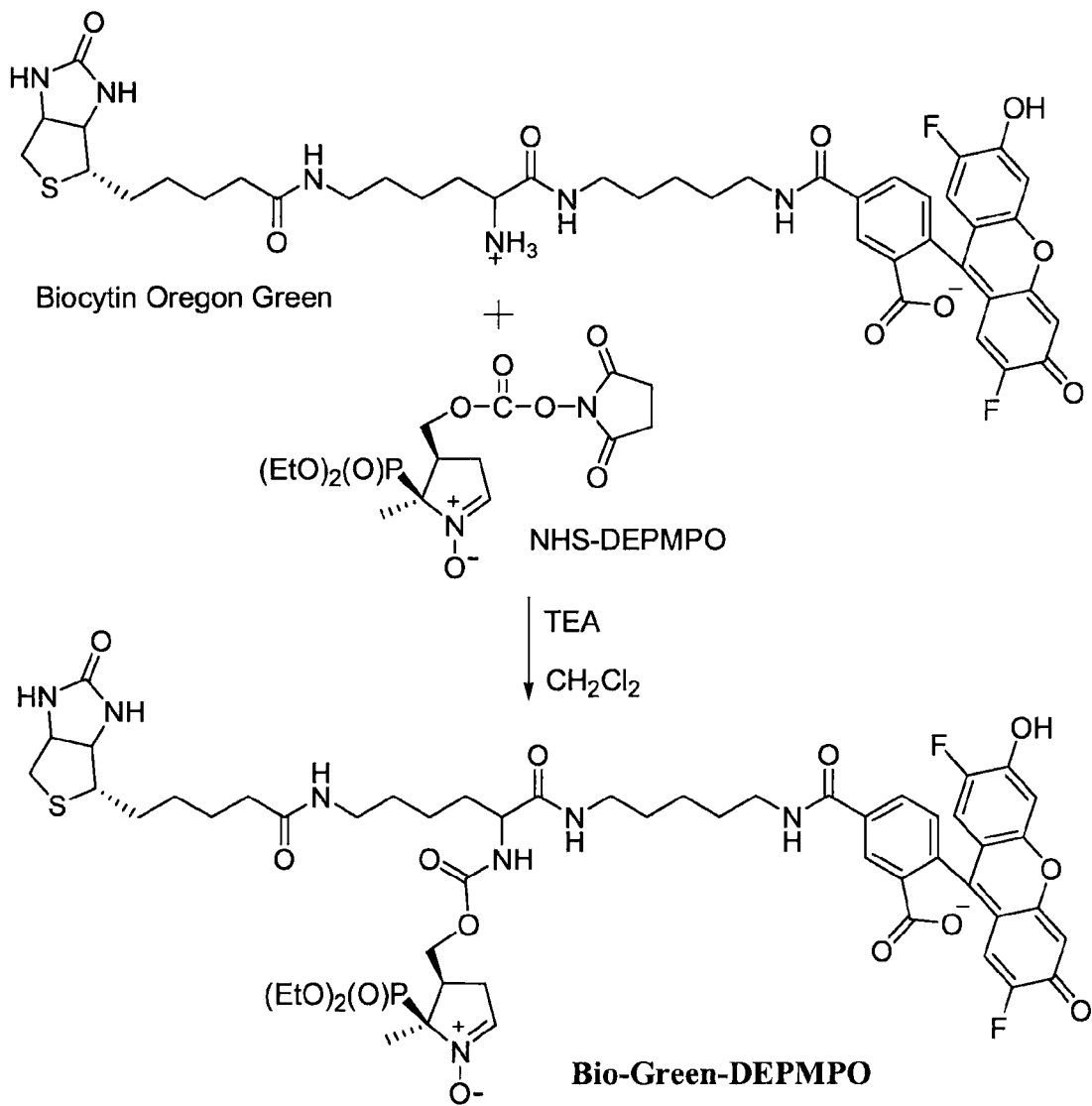
Figure 8:
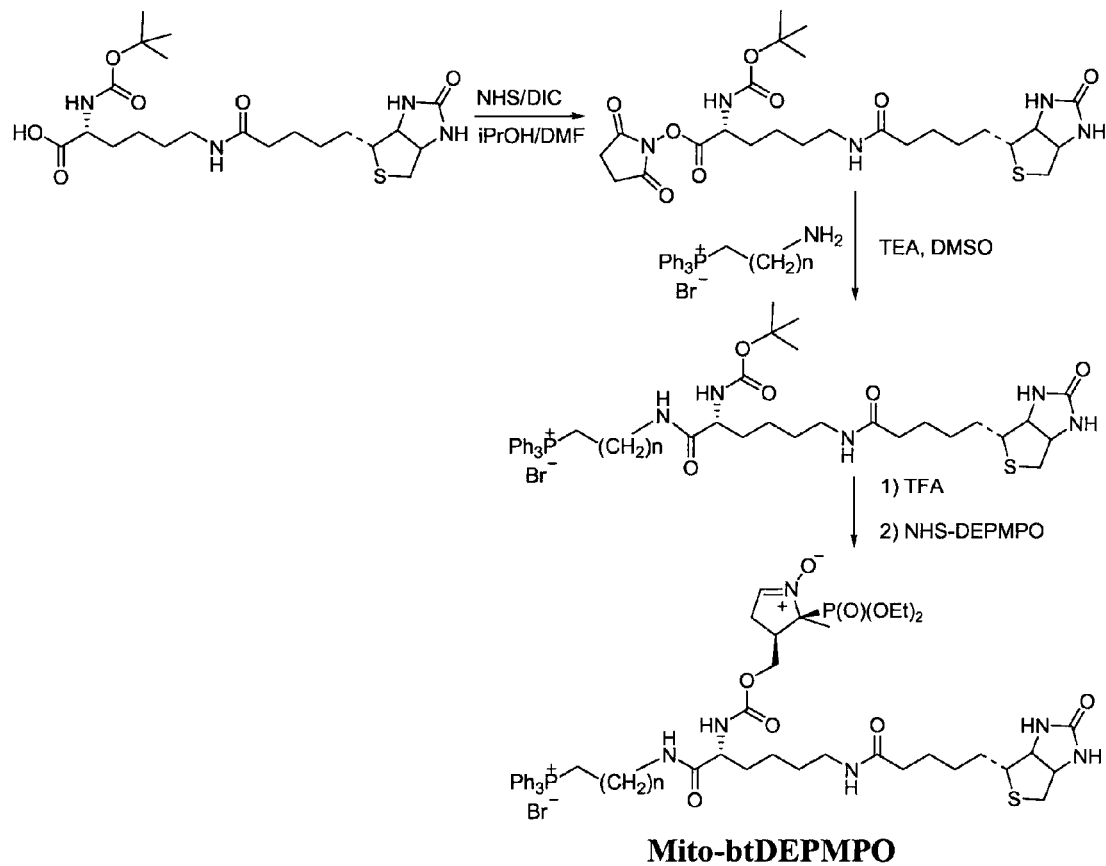

FIG. 4A-B show a time course of a spectra recorded by EPR using SVD analysis after photolysis of a solution containing BSA-SNO and btDEPMPO (A) or BSA and btDEPMPO (B);

FIG. 5 shows a Western blot analysis of BSA-SNO after photolysis in the presence of biotin-DEPMPO (lane 1, BSA-SNO with biotin-DEPMPO; lane 2, BSA with biotin-DEPMPO; lane 3, BSA with biotin-IAA);

FIG. 6 shows a Western blot analysis of cellular S-nitrosated proteins (lane 1, biotinylated BSA; lane 2, biotinylated total cellular protein; lane 3, CysNO-treated cells (5 μg protein); lane 4, CysNO-treated cells (10 μg protein); lane 5, untreated cells (5 μg protein); lane 6, untreated cells (10 μg protein));

FIG. 7 shows a diagram for the synthesis of one embodiment of a trifunctional spin trapping compound, Bio-Green-DEPMPO; and FIG. 8 shows a diagram for the synthesis of another embodiment of a trifunctional spin trapping compound, mito-btDEPMPO.

Figure 9:
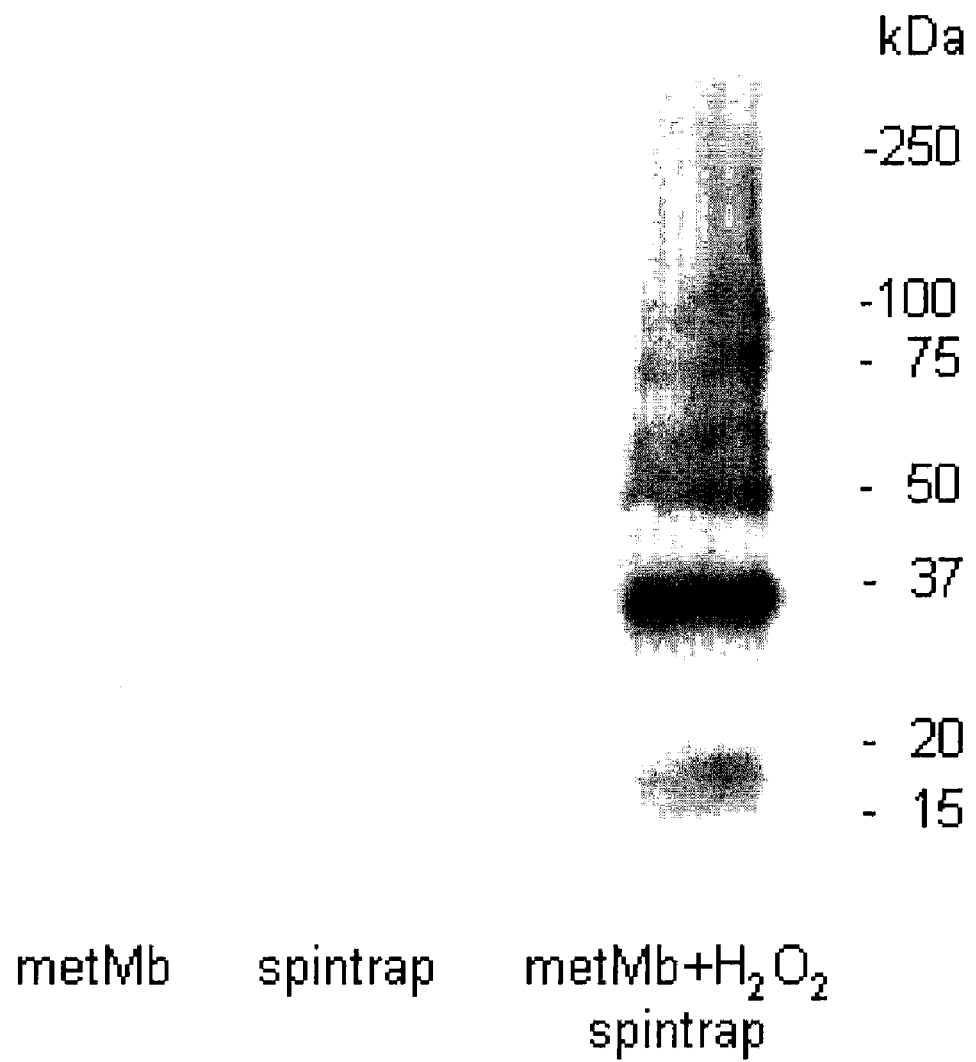

FIG. 9 shows a Western blot analysis of a gel using biotin-DEPMPO with $H_2O_2$-treated MetMb.

Figure 10:
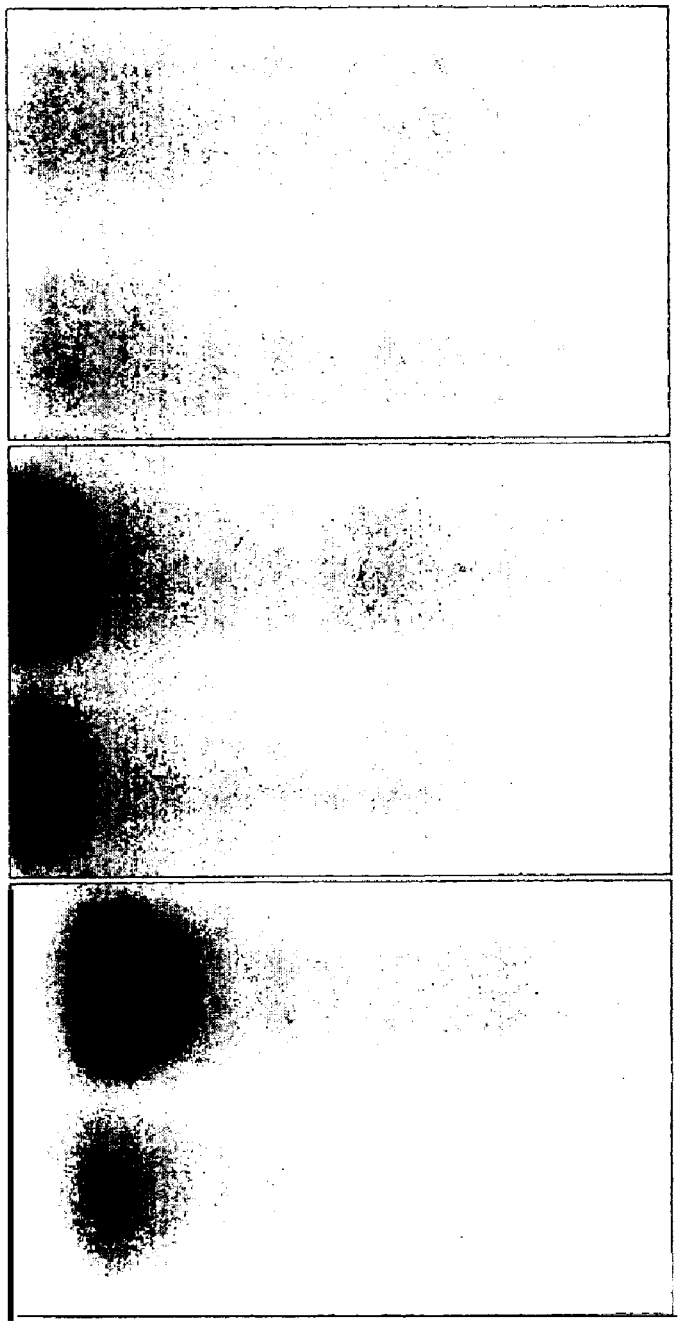

FIG. 10 shows spintrap data obtained using BioGreen-DEPMPO with $H_2O_2$ (or nitrite) treated with OxyHb, MetMb or Mb.

While the invention is susceptible to various modifications and alternative forms, specific embodiments thereof are shown by way of example in the drawings and are herein described in detail. It should be understood, however, that the description of specific embodiments is not intended to limit the invention to the particular forms disclosed, but on the contrary, the intention is to cover all modifications, equivalents and alternatives falling within the spirit and scope of the invention as defined by the appended claims.

DESCRIPTION OF EXEMPLARY EMBODIMENTS

Of particular interest herein is the analysis of free radicals derived from reactive oxygen species (ROS; e.g., superoxide ($O_2.^-$) hydrogen peroxide ($H_2O_2$), hydroxyl radical (.OH)), reactive nitrogen species (RNS; e.g., nitric oxide (NO)) and reactive sulfur species (RSS; e.g., thiols (—SH)). As such, one can detect protein free radicals such as R—OO., R—O., R—C., R—S. and R—SS., where R is a protein. Likewise, one can detect lipid free radicals such as lipid peroxyl (ROO.) and alkoxyl (RO.) radicals, where R is a lipid. Moreover, one can detect nucleic acid free radicals.

Detection of free radicals by EPR depends upon the formation of a persistent nitroxide from a reaction of a nitrone with a free radical. Nitroxides, however, have a limited lifetime and are either reduced to a hydroxylamine adduct or oxidized back to a nitrone adduct, both of which cannot be detected by EPR. The analysis of free radicals can be improved by using compounds and methods that directly analyze spin adducts without exclusively relying upon stability of the nitroxide. A spin adduct is a product of a direct addition of two distinct molecules (i.e., spin trap compound+ free radical), resulting in a single reaction product containing all atoms of all components, with formation of a covalent bond and a net reduction in bond multiplicity in at least one of the reactants.

Nitrones are N-oxides of an imine (i.e., a functional group having a carbon-nitrogen double bond), and can have a cyclic structure. With respect to the nitrones of Formulas 1 and 2, $R_1$, $R_2$, $R_3$, $R_4$, $R_5$, $R_6$ and $R_7$ may independently be one of the following: deuterium, hydrogen, hydrocarbon (e.g., alkyl, alkenyl, alkynyl, phenyl or benzyl), haloalkane (e.g., bromoalkane, iodoalkane, fluoroalkane or chloroalkane), oxygen-containing group (e.g., acyl halide, alcohol, ketone, aldehyde, carbonate, carboxylate, carboxylic acid, ether, ester, hydroperoxide or peroxide), nitrogen-containing group (e.g., amide, amine, imine, imide, azide, azo compound, cyanate, isocyanate, nitrate, nitrile, nitrite, nitro compound, nitroso compound or pyridine derivative), or phosphorus- and sulfur-containing group (e.g., phosphine, phosphonate, phosphodiester, phosphonic acid, phosphate, sulfide, sulfone, sulfonic acid, sulfoxide, thiol, thiocyanate or disulfide), as well as suitable combinations thereof.

Exemplary nitrones of Formula 1 include, but are not limited to: N-tert-butyl-alpha-phenyl nitrone (PBN), alpha-(4-pyridyl 1-oxide)-N-tert butylnitrone (POBN) and 2'-sulfonyl PBN (SPBN).

Exemplary nitrones of Formula 2 include, but are not limited to: 5-(diethoxy-phosphoryl)-5-methyl-1-pyrroline-N-oxide (DEPMPO), 5-tert-butoxycarbonyl 5-methyl-1-pyrroline N-oxide (BMPO), 5-(diisopropoxyphosphoryl)-5-methyl-1-pyrroline-N-oxide (DIPPMO), 5-ethoxycarbonyl-5-methyl-1-pyrroline N-oxide (EMPO), 5-carbamoyl-5-methyl-1-pyrroline N-oxide (AMPO), 5,5-dimethyl-1-pyrroline 1-oxide (DMPO), 5-(dipropoxyphosphoryl)-5-methyl-1-pyrroline N-oxide (DPPMPO), 5-(di-n-butoxyphosphoryl)-5-methyl-1-pyrroline N-oxide (DBPMPO) and 5-(bis-(2-ethylhexyloxy)phosphoryl)-5-methyl-1-pyrroline N-oxide (DEHPMPO). Of particular interest herein are DEPMPO, DIPPMO and BMPO, which have the following structures:

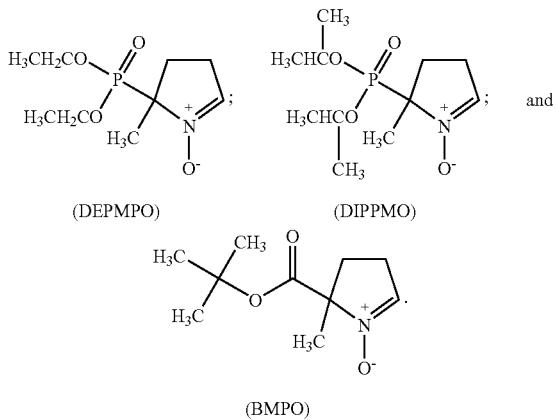

(DEPMPO)    (DIPPMO)

(BMPO)

The linker (L) may be a hydrocarbon, a polyester, a polyethylene glycol, a carbohydrate, a fluorocarbon, a nucleic acid, a peptide, a polyamine, an amino acid or a combination thereof. The linker joins the detection moiety to the nitrone. The linker further joins the targeting moiety, if present, to the nitrone. The linker may be attached to the nitrone at one any of $R_1$, $R_2$, $R_3$, $R_4$, $R_5$, $R_6$ and $R_7$ on Formula 1 or 2.

The detecting moiety (D) is an agent that can be linked to the linker and that can be used to detect the nitrone following spin trapping. The detecting moiety is not affected by the redox state of the nitrone or by the free radical and is therefore stable. The detecting moiety may be a small molecule, a chromogenic molecule, a fluorescent molecule or a radioactive molecule. Small molecules include, but are not limited to, biotin, a positron emission tomography (PET) radiotracer, a single photon emission computed tomography (SPECT) radiotracer and other suitable small molecules. Also contemplated are contrast agents for radiotracers (e.g., gadolinium-tetraazacyclododecanetetraacetic (Gd-DOTA), gadolinium-diethylenetriamine penta-acetic acid (Gd-DTPA)). Biotin has the following structure:

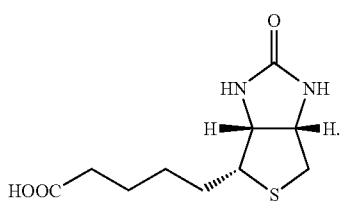

Chromogenic molecules include, but are not limited to, luminescent labels (e.g., luminol), enzymatic labels (e.g., horseradish peroxidase, beta-galactosidase, luciferase, alkaline phosphatase and acetylcholinesterase), 7-methoxycoumarin derivatives, carboxyfluorescein derivatives, ethidium bromide derivatives, EVOblue derivatives and Dabcyl derivatives, and other suitable chromogenic molecules.

Fluorescent molecules include, but are not limited to, fluorescein dyes (e.g., fluorescein isothiocyanate (FITC), rhodamine, lanthanide phosphors, Cascade Blue® (CB), Lucifer yellow, 5(and 6)-tetramethylrhodamine, Oregon Green®, Tokyo Green, carboxynaphthofluorescein, carboxyseminaphthofluorescein (SNAFL) and the Alexa Fluor family of dyes, as well as other cyanine dyes).

Radioactive molecules include, but are not limited to, $^{277}Ac$, $^{105}Ag$, $^{198}Au$, $^{128}Ba$, $^{131}Ba$, $^{7}Be$, $^{204}Bi$, $^{205}Bi$, $^{206}Bi$, $^{76}Br$, $^{77}Br$, $^{82}Br$, $^{11}C$, $^{14}C$, $^{47}Ca$, $^{109}Cd$, $^{36}Cl$, $^{48}Cr$, $^{51}Cr$, $^{62}Cu$, $^{64}Cu$, $^{67}Cu$, $^{165}Dy$, $^{155}Eu$, $^{18}F$, $^{52}Fe$, $^{55}Fe$, $^{66}Ga$, $^{67}Ga$, $^{72}Ga$, $^{153}Gd$, $^{3}H$, $^{106}Ho$, $^{111}I$, $^{123}I$, $^{125}I$, $^{131}I$, $^{111}In$, $^{113}In$, $^{115}In$, $^{123}I$, $^{125}I$, $^{131}I$, $^{189}Ir$, $^{191}Ir$, $^{192}Ir$, $^{194}Ir$, $^{42}K$, $^{177}Lu$, $^{22}Na$, $^{24}Na$, $^{15}O$, $^{191m-191}Os$, $^{109}Pd$, $^{32}P$, $^{33}P$, $^{226}Ra$, $^{82m}Rb$, $^{186}Re$, $^{188}Re$, $^{35}S$, $^{38}S$, $^{46}Sc$, $^{47}Sc$, $^{72}Se$, $^{75}Se$, $^{153}Sm$, $^{113}Sn$, $^{117m}Sn$, $^{121}Sn$, $^{89}Sr$, $^{177}Ta$, $^{96}Tc$, $^{99m}Tc$, $^{201}Tl$, $^{202}Tl$, $^{88}Y$, $^{90}Y$, $^{166}Yb$, $^{169}Yb$, $^{175}Yb$, $^{62}Zn$ and $^{65}Zn$.

Exemplary bifunctional spin trapping compounds having a biotin detection moiety include compounds of Formula 3 and Formula 4:

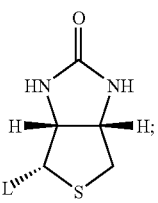

(Formula 3)

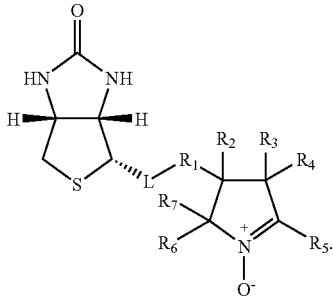

(Formula 4)

As noted above, $R_1$, $R_2$, $R_3$, $R_4$, $R_5$, $R_6$ and $R_7$, may independently be one of the following: deuterium, hydrogen, hydrocarbon (e.g., alkyl, alkenyl, alkynyl, phenyl or benzyl); halogenalkane (e.g., bromoalkane, iodoalkane, fluoroalkane or chloroalkane), oxygen-containing group (e.g., acyl halide, alcohol, ketone, aldehyde, carbamate, carboxylate, carboxylic acid, ether, ester, hydroperoxide or peroxide), nitrogen-containing group (e.g., amide, amine, imine, imide, azide, azo compound, cyanate, isocyanate, nitrate, nitrile, nitrite, nitro compound, nitroso compound or pyridine derivative), or phosphorus- and sulfur-containing group (e.g., phosphine, phosphonate, phosphodiester, phosphonic acid, phosphate, sulfide, sulfone, sulfonic acid, sulfoxide, thiol, thiocyanate or disulfide), as well as suitable combinations thereof.

The linker (L) may be a hydrocarbon, a polyester, a polyethylene glycol, a carbohydrate, a fluorocarbon, a nucleic acid, a peptide, a polyamine, an amino acid or a combination thereof. The linker joins the detection moiety to the nitrone and may be attached to the nitrone at one any of $R_1$, $R_2$, $R_3$, $R_4$, $R_5$, $R_6$ and $R_7$ on Formulas 1-4.

The compounds described herein can further include a targeting moiety (T). The targeting moiety is an agent that can be linked to a nitrone and that can be used to direct the nitrone to an organ, a cell, an organelle or even a molecule of interest. The targeting moiety may be linked to the linker or may be linked directly to the nitrone, as in Formulas 1-4 at $R_1$, $R_2$, $R_3$, $R_4$, $R_5$, $R_6$ and $R_7$. The targeting moiety is specific for an organ, a cell, an organelle or a molecule of interest. Targeting moieties include, but are not limited to, organ targeting agents, cell targeting agents, organelle targeting agents and molecule targeting agents. It is understood by one of ordinary skill in the art that some targeting moieties may fall into one or more groups of targeting agents. Likewise, it is understood by one of ordinary skill in the art that some of the detecting moieties may be a targeting moiety (e.g., biotin).

Organ targeting agents include, but are not limited to, lectins, peptides, sugars and molecules that recognize cell surface markers (e.g., antibodies and RGD peptides). See, e.g., Chalier F, et al., Org. Biomol. Chem. 2:927-934 (2004), incorporated herein by reference as if set forth in its entirety.

Cell targeting agents include, but are not limited to, cell-penetrating agents, receptor targeting agents and other cell surface targeting agents. See, e.g., Chalier et at., supra; Hay A, et al., Arch. Biochem. Biophys. 435:336-346 (2005); Liu Y, et al., Chem. Commun. (Camb) 39:4943-4945 (2005); and Ouari O, et al., J. Org. Chem. 64:3554-3556 (1999), each of which is incorporated herein by reference as if set forth in its entirety.

Other cell targeting agents are known and may be used with the nitrones described herein. See, e.g., McCusker C, et al., J. Immunol. 179:2556-2564 (2007); Marshall N, et al., J. Immunol. Methods 325:114-126 (2007); Wu R, et al., Nucleic Acids Res. 35:5182-5191 (2007); Toshchakov V & Vogel S, Expert Opin. Biol. Ther. 7:1035-1050 (2007); Slofstra S, et al., Blood 110:3176-3182 (2007); Weiss H, et al., Chem Biodivers. 4:1413-1437 (2007); Moulton H, et al., Biochem. Soc. Trans. 35:826-828 (2007); Chen L & Harrison S, Biochem. Soc. Trans. 35:821-825 (2007); Torchilin V, et al., Biochem. Soc. Trans. 35:816-820 (2007); and Moschos S, et al., Biochem. Soc. Trans. 35:807-810 (2007), each of which is incorporated herein by reference as if set forth in its entirety.

Exemplary cell-penetrating peptides include, but are not limited to, Penetratin®, HIV-1 Tat protein, HIV-1 Rev protein, Arg9 (polyarginine), pIs1-1, a membrane-translocating sequence (MTS; see, Fawell S, et al., Proc. Natl. Acad. Sci. USA 91:664-668 (1994)), an integrin h-region, a multiple antigenic peptide (MAP; see, Tam J, Proc. Natl. Acad. Sci. USA, 85:5409-5413 (1988).), Herpes Simplex Virus VP22 protein, Influenza Virus HA-2 protein and Bac (1-15, 15-24). Generally, cell-penetrating peptides are short polycationic polypeptides.

Exemplary receptor targeting agents include, but are not limited to, folate derivatives (e.g., pteoric acid or folic acid), integrin ligands (e.g., RGD peptides) and antibodies to cell surface markers. See, e.g., Vlahov I, et al., J. Org. Chem. 72:5968-5972 (2007), Reddy J, et al., Cancer Res. 67: 4434-4442 (2007); Yang J, et al., J. Pharmacol. Exp. Ther. 321:462-468 (2007); Lu Y, et al., Mol. Cancer Ther. 5:3258-3267 (2006); Knutson K, et al., J. Clin. Oncol. 24:4254-4261 (2006), Yang J, et al., Proc. Natl. Acad. Sci. USA 103:13872-13877 (2006); Lu Y, et al., Adv. Drug Deliv. Rev. 56:1161-1176 (2004), Leamon C, et al., Bioconjugate Chem. 17:1226-1232 (2006), Vlahov I, et al., Bioorg. Med. Chem. Lett. 16:5093-5096 (2006); Reddy J, et al., Cancer Chemother. Pharmacol. 58:229-236 (2006); Leamon C, et al., Bioconj. Chem. 16:803-811 (2005); and Parker N, et al., Anal. Biochem. 338:284-293 (2005), each of which is incorporated herein by reference as if set forth in its entirety. Other receptor targeting agents include bombesin, chlorotoxin, tamoxifen, taxol and the like.

Organelle targeting agents include, but are not limited to, agents that target a nucleus (e.g., acridine-based nuclear-targeting agents, oligonucleobases, steroid hormones (or analogs thereof) or any other nuclear localization signal, such as Pro-Pro-Lys-Lys-Lys-Arg-Lys-Val-), agents that target a nucleolus (e.g., human I-mfa domain-containing protein (HIC) p40, Hepatitis δ antigen, a nucleolar targeting signal from human T-cell leukemia virus type I Rex-encoded protein, a nucleolar targeting signal from the Werner syndrome protein or any other nucleolar localization signal), agents that target a mitochondria (or a chloroplast, e.g., any mitochondrial targeting signal, such as $H_2N$-Met-Leu-Ser-Leu-Arg-Gln-Ser-Ile-Arg-Phe-Phe-Lys-Pro-Ala-Thr-Arg-Thr-Leu-Cys-Ser-Ser-Arg-Tyr-Leu-Leu-), agents that target an endoplasmic reticulum (e.g., any endoplasmic reticulum localization signal, such as $H_2N$-Met-Met-Ser-Phe-Val-Ser-Leu-Leu-Leu-Val-Gly-Ile-Leu-Phe-Trp-Ala-Thr-Glu-Ala-Glu-Gln-Leu-Thr-Lys-Cys-Glu-Val-Phe-Gln-), agents that target a Golgi apparatus and agents that target peroxisomes (e.g., any peroxisomal targeting signal, such as -Ser-Lys-Leu-COOH or $H_2N$-Arg-Leu-$X_5$-His-Leu-, where $X_5$ is any five amino acids) or other vesicles.

Of particular interest herein are agents that target the mitochondria. See, e.g., Murphy M, et al., J. Biol. Chem. 278: 48534-48545 (2003); Smith R, et al., Proc. Natl. Acad. Sci. USA. 100:5407-5412 (2003); and Hardy M, et al., Chem. Commun. (Camb) 10: 1083-1085 (2007), each of which is incorporated herein by reference as if set forth in its entirety. Exemplary mitochondria targeting agents include, but are not limited to, a triphenylphosphonium (TPP) cation, a pyridinium cation or a tetraalkyl ammonium cation, which have the following structures:

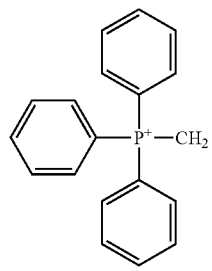

(triphenylphosphonium cation);

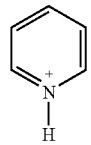 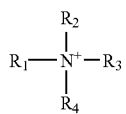

(pyridinium cation); and (tetraalkyl ammonium cation), where $R_1$, $R_2$, $R_3$ and $R_4$ are independently a $C_{1-12}$ unbranched or branched, linear or non-linear alkyl, such as methyl groups, ethyl groups, propyl groups, butyl groups, pentyl groups, hexyl groups, heptyl groups, octyl groups, nonyl groups, decyl groups, undecyl groups or dodecyl groups.

Other mitochondria targeting agents are known and may be used with the nitrones described herein. See, e.g., Murphy M & Smith R, Annu. Rev. Pharmacol. Toxicol. 47:629-656 (2007). Ross M, et al., Biochem. J. 400:199-208 (2006); James A, et al., J. Biol. Chem. 280:21295-21312 (2005); Filipovska A, et al., J. Biol. Chem. 280:24113-24126 (2005); Adlam V, et al., FASEB J. 19:1088-1095 (2005); Blaikie F, et al., Biosci. Rep. 26:231-243 (2006), each of which is incorporated herein by reference as if set forth in its entirety.

Molecule targeting agents include, but are not limited to, agents that target a specific molecule, such as affinity reagents (e.g., Fabs, biotin and hexa-histidine (His6) tags). In general, molecule targeting agents can be used to purify or separate the spin adduct from samples. That is, a trifunctional spin trapping compound having biotin can be purified from a sample via immunoprecipitation or avidin. As noted above, biotin can function as a detection moiety in some trifunctional spin trapping compounds or as a molecule targeting agent in others.

Exemplary trifunctional spin trapping compounds having a biotin detection moiety include compounds of Formula 5 or Formula 6:

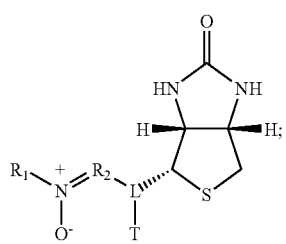

(Formula 5)

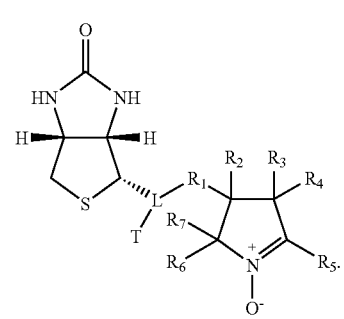

(Formula 6)

Exemplary trifunctional spin trapping compounds having a biotin targeting moiety include compounds of Formula 7 or Formula 8.

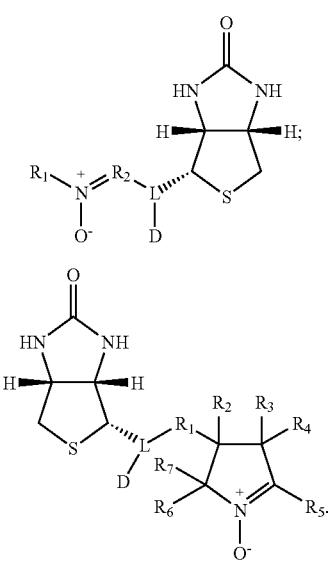

As noted above, $R_1$, $R_2$, $R_3$, $R_4$, $R_5$, $R_6$ and $R_7$, may independently be one of the following: deuterium, hydrogen, hydrocarbon (e.g., alkyl, alkenyl, alkynyl, phenyl or benzyl); haloalkane (e.g., bromoalkane, iodoalkane, fluoroalkane or chloroalkane), oxygen-containing group (e.g., acyl halide, alcohol, ketone, aldehyde, carbonate, carboxylate, carboxylic acid, ether, ester, hydroperoxide or peroxide), nitrogen-containing group (e.g., amide, amine, imine, imide, azide, azo compound, cyanate, isocyanate, nitrate, nitrile, nitrite, nitro compound, nitroso compound or pyridine derivative), or phosphorus- and sulfur-containing group (e.g., phosphine, phosphonate, phosphodiester, phosphonic acid, phosphate, sulfide, sulfone, sulfonic acid, sulfoxide, thiol, thiocyanate or disulfide), as well as suitable combinations thereof.

As noted above, the linker (L) may be a hydrocarbon, a polyester, a polyethylene glycol, a carbohydrate, a fluorocarbon, a nucleic acid, a peptide, a polyamine, an amino acid or a combination thereof. The linker joins the detection moiety and the targeting moiety to the nitrone. The linker may be attached to the nitrone at one any of $R_1$, $R_2$, $R_3$, $R_4$, $R_5$, $R_6$ and $R_7$.

Methods of detecting spin adducts include enzyme-linked immunosorbent assays (ELISA), fluorescence microscopy, fluorescence spectroscopy, Northern blot analysis, Southern blot analysis, Western blot analysis and Immunodot assays. See, e.g., Mason R, Free Radic. Biol. Med. 36:1214-1223 (2004). Other methods for detecting spin adducts include high performance liquid chromatography (HPLC), mass spectrometry (MS), magnetic resonance imaging (MRI), positron emission tomography (PET) and single photon emission computed tomography (SPECT). Moreover, EPR can be used to detect the spin adducts.

The invention will be more fully understood upon consideration of the following non-limiting Examples.

EXAMPLES

Example 1

Bifunctional Spin Trap Compound

Methods: btDEPMPO was synthesized as follows: a solution of biotinylamidopropylammonium trifluoroacetate (0.0665 g, 0.22 mmol; Sigma; St. Louis, Mo.) and of triethylamine (0.034 mL, 0.24 m-mol; Sigma) in 3 mL dimethyl sulfoxide (DMSO; Sigma) were added at room temperature under inert atmosphere to a solution of 5-diethoxyphosphoryl-4-succinimidyloxycarbonyloxymethyl-5-methyl-1-pyrroline-N-oxide (NHS-DEPMPO) (0.090 g, 0.22 mmol) in DMSO (2 mL). The reaction mixture was stirred for 24 hours at room temperature, and brine (5 mL) was added. An organic layer was separated and the expected nitrone was extracted again twice from the aqueous phase with $CH_2Cl_2$ (10 mL). The mixed organic phases were dried with $Na_2SO_4$, and the solvent was removed under reduced pressure. A crude product that was composed mainly of the expected nitrone from NMR ($^1H$ and $^{31}P$) analysis was purified by flash chromatography on silicagel with a gradient of ethanol (15 up 100%) in $CH_2Cl_2$ and to obtain btDEPMPO. See, Hardy et al., supra.

Results: btDEPMPO was obtained as a white powder (51 mg, 0.087 mmol) with 39% yield; melting point 176° C. (decomposition). $^{31}P$ NMR (81.01 MHz) δ 21.33. $^1H$ NMR (200.13 MHz; $CD_3OD$; $Me_4Si$) δ 7.28 (1H, q, J=3.0, 3.0), 4.56-4.38 (2H, m), 4.37-4.13 (6H, m), 3.27-3.10 (5H, m), 2.95 (1H, d, J=12.9), 2.70 (1H, dd, J=12.9, 4.9), 2.87-2.61 (3H, m), 2.22 (2H, t), 1.74 (3H, d, J=14.4), 1.76-1.42 (8H, m), 1.37 (6H, 2t, J=7.0, 7.2). $^{13}C$ NMR (50.32 MHz) δ 176.2 (1C, s), 166.0 (1C, s), 158.4 (1C, s), 140.7 (1C, d, J=5.7), 77.5 (1C, d, J=151.5), 66.0 (1C, d, J=6.6), 64.9 (1C, d, J=7.7), 64.9 (1C, s), 63.4 (1C, s), 61.7 (1C, s), 57.0 (1C, s), 47.3 (1C, s), 41.0 (1C, s), 39.2 (1C, s), 37.7 (1C, s), 36.8 (1C, s), 31.5 (1C, s), 30.6, 29.7, 29.5, 26.9 (4C, 4s), 20.7 (1C, s) 16.7, 16.7 (2C, 2d, J=5.7). HRMS calculated for $[C_{24}H_{42}N_5O_8PS+H]^+$ 592.2570, found: 592.2529. ESI-MS/MS (20 eV) m/z (%) 592.4 (100) ($M^+$+H), 574 (5), 436 (4), 327 (17), 301 (45), 284 (5), 266 (5), 248 (10), 230 (8), 218 (14), 138 (5).

Example 2

Detection of Protein and Non-Protein Free Radicals with Bifunctional Spin Trap Compounds Methods: All materials were purchased from Sigma-Aldrich (St. Louis, Mo.) unless otherwise indicated.

BSA-SNO: BSA-SNO was prepared according the method of Katsumi et al. by incubating BSA with S-nitrosocysteine, followed by purification on a Sephadex® G-25 size-exclusion column. Katsumi H, et al., J. Pharm. Sci. 93:2343-2352 (2004), incorporated herein by reference as if set forth in its entirety.

btDEPMPO: The bifunctional spin trap compound, btDEPMPO, was prepared as described above in Example 1.

EPR: EPR was conducted on a X-band Bruker EMX Spectrometer (Bruker BioSpin Corp.; Billerica, Mass.).

Detection of protein radicals: Myoglobin (400 μM) was incubated with hydrogen peroxide ($H_2O_2$, 5 mM) in the presence of btDEPMPO (20 mM) using a method adapted from Kelman et al. Kelman D, et al., J. Biol. Chem. 269:7458-7463 (1994), incorporated herein by reference as if set forth in its entirety. The protein was separated by SDS-PAGE and analyzed by Western blot analysis using an alkaline phosphotase-conjugated, anti-biotin antibody (1:2000).

Detection of protein S-nitrosation and thiyl radicals: BSA-SNO was generated by incubating BSA with S-nitrosocysteine followed by separation on a Sephadex® G25 Size-Exclusion Column. BSA-SNO (5 mg/ml) was incubated with with btDEPMPO (20 mM) under irradiation by UV/visible light passed through a 400 nm cut-off filter for 20 minutes. During this time, light homolyzed the S—N bond of the S-nitrosothiols to generate a thiyl radical that was trapped by btDEPMPO, thus permitting Western blot analysis of S-nitrosated proteins. All solutions were bubbled with argon to remove oxygen. After irradiation, protein was separated by sodium dodecyl sulphate (SDS) polyacrylamide gel electrophoresis and was then blotted to nitrocellulose membranes. Protein was detected using an anti-biotin antibody directly linked to horse radish peroxidase (Calbiochem; San Diego, Calif.), thereby removing the requirement for a secondary antibody, and developed using an enhanced chemiluminescence (ECL) reagent (Pierce; Rockford, Ill.).

Detection of S-nitrosated proteins in RAW 264.7 cells: Briefly, murine macrophage-like RAW 264.7 cells (American Type Culture Collection (ATCC); Manassas, Va.) were grown to confluence in a 10 cm plate and then incubated with S-nitrosocysteine (200 µM) for 1 hour to generate an intracellular protein S-nitrosation level of ~5 mg/ml) in a method adapted from Zhang & Hogg. Zhang Y & Hogg N, Proc. Natl. Acad. Sci. USA 101:7891-7896 (2004), incorporated herein by reference as if set forth in its entirety. Following incubation, the cells were lysed, and btDEPMPO was added to the resulting mixture. This mixture was then irradiated under the same conditions described above for BSA-SNO. After irradiation, proteins were separated by SDS-PAGE prior to Western blot analysis.

Results: With respect to protein radicals, btDEPMPO trapped this protein radical to give an EPR signal, indicating that the biotin group did not interfere with the ability of the cyclic nitrone to trap the protein radical. Western blot analysis of the spin-trapped protein radical was performed along with appropriate controls. While no bands were detected in the absence of btDEPMPO or $H_2O_2$, the complete system gave a strong band at the molecular weight of myoglobin (~17 kDa), indicating that btDEPMPO was able to trap the protein radical and that the spin adduct was stable enough to be detected by Western blot analysis. The covalent association between btDEPMPO and the protein radical was confirmed by mass spectrometry (17542.3).

With respect to BSA S-nitrosation, btDEPMPO trapped the thiyl radical generated after photolysis of BSA-NO to give an EPR signal, indicating that the biotin group did not interfere with the ability of the cyclic nitrone to trap the protein radical. While the EPR spectrum had a limited life-time because of both reduction and oxidation of the nitroxide, biotin remained stably associated with the protein thiol and was detected by Western blot analysis. Biotin labeling can also allow immunoprecipitation of proteins and analysis by MS.

During photolysis, a broad EPR signal was observed that grew in time, until the light was switched off, at which point the signal slowly decayed. No such EPR signals were observed with BSA alone, indicating specificity for the S-nitroso group. During photolysis of BSA-SNO, a complex multi-line EPR signal evolved over time, indicating that btDEPMPO trapped the radicals generated after photolysis of BSA-SNO. Photolysis of BSA resulted in a broad, non-specific signal that did not change intensity as a function of time.

With respect to the RAW 264.7 cells, these cells were used to test if btDEPMPO could be applied to complex mixtures of S-nitrosated proteins. Biotin remained stably associated with protein thiols and was detected by Western blot analysis. While no bands were detected in the absence of btDEPMPO, the complete system detected many proteins in the CysNO-treated cells, but not in the cells that had not been treated with CysNO. These results indicated that non-specific labeling was low, and that the photolysis/biotinylation method detected a large range of S-nitrosated proteins.

Example 3

Trifunctional Spin Trap Compound

Methods: Bio-Green-DEPMPO was synthesized as follows: a solution of biocytin Oregon Green® (10 mg, 0.012 mmol; Invitrogen) and of triethylamine (4 µL, 0.030 mmol; Sigma) in 2 ml dimethyl sulfoxide (DMSO; Sigma) were added at room temperature under inert atmosphere to a solution of 5-diethoxyphosphoryl-4-succinimidyloxycarbonyloxymethyl-5-methyl-1-pyrroline-N-oxide (NHS-DEPMPO) (5 mg, 0.013 mmol) in DMSO (2 mL). The reaction mixture was stirred for 6 hours at room temperature. The solvent was removed under reduced pressure, and a crude product was purified by preparative HPLC using a $C_{18}$ column that was equilibrated with 10% $CH_3CN$ (containing 0.1% (v/v) trifluoroacetic acid (TFA) in 0.1% TFA aqueous solution) to afford Bio-Green-DEPMPO.

Results: Bio-Green-DEPMPO was obtained as a orange powder (12 mg, 90% of yield). HPLC, 22.8 min. HRMS calculated for $C_{53}H_{66}F_2N_7O_{15}PS$, $[C_{53}H_{66}F_2N_7O_{15}PS]^+$+$H^+$: 1142.3971, found: 1142.3092.

Example 4

Trifunctional Spin Trap Compound

Methods: Mito-btDEPMPO is synthesized as follows: N-hydroxysuccinimide (0.044 g, 0.382 mmol) and DCC (0.052 mL, 0.35 mmol) are added to a cloudy mixture of N-t-Boc-biocytin (0.15 g, 0.326 mmol; Invitrogen) in isopropyl alcohol/DMF (10 ml). After 12 hours, the solvents are removed under vacuum and dissolved in $CHCl_3$. A resulting solution is added dropwise to ethyl ether/hexane (1:1). A resulting white precipitate is collected and is dried under vacuum to give 0.17 g (93%) NHS—N-t-Boc-biocytin.

A solution of amino-TPP and triethylamine in DMSO is added at room temperature and under inert atmosphere to a solution of NHS—N-t-Boc-biocytin in DMSO (2 ml). A reaction mixture is stirred for 6 hours at room temperature. Solvent is removed under reduced pressure, and a crude product is purified by preparative HPLC using a C18 column equilibrated with 10% $CH_3CN$ (containing 0.1% (v/v) trifluoroacetic acid (TFA) in 0.1% TFA aqueous solution) to give TPP—N-t-Boc-biocytin.

After removal of the t-Boc protecting group by TFA, NHS-DEPMPO is added to a solution of the TPP—$NH_2$-biocytin in the presence of TEA in DMSO. Solvent is removed and a product is purified by preparative HPLC using a $C_{18}$ column equilibrated with 10% $CH_3CN$ (containing 0.1% (v/v) trifluoroacetic acid (TFA) in 0.1% TFA aqueous solution) to afford Mito-btDEPMPO.

Example 5 (Prophetic)

Detection of Protein and Non-Protein Free Radicals with Trifunctional Spin Trap Molecules Methods: All materials were purchased from Sigma-Aldrich unless otherwise indicated.

Trifunctional Spin Trap Compound: The trifunctional spin trap compound was prepared as described above in Example 3 or 4.

EPR: EPR was conducted as described above in Example 2.

Detection of S-nitrosated proteins and thiyl radicals in RAW 264.7 cells: RAW 264.7 cells were incubated were incubated with S-nitrosocysteine for 1 hour, as described above in Example 2. Following incubation, the cells were lysed, and Bio-Green-DEPMPO or mito-btDEPMPO was added to the resulting mixture. This mixture was then irradiated under the same conditions described above. After irradiation, proteins were isolated and separated by SDS-PAGE prior to Western blot analysis. In some instances, mitochondria were isolated prior to Western blot analysis or detection using a fluorescence scanner (Typhoon™ Trio; GE Healthcare; Piscataway, N.J.).

Results: Bio-Green-DEPMPO trapped this protein radical to give an EPR signal, indicating that neither the biotin group nor the Oregon Green® group interfere with the ability of the cyclic nitrone to trap the protein radical. Proteins were immuno-precipitated using an anti-biotin antibody. Precipitated proteins were separated by SDS-polyacrylamide gel electrophoresis using gels cast in low-fluorescent glass plates (Jule Biotechnologies, Inc.; Milford, Conn.) and directly scanned using a Typhoon™ Trio fluorescence scanner. The detection of fluorescently tagged proteins shows that Bio-Green-DEPMPO can trap protein radicals, that the biotin moiety allows for the separation of tagged proteins from unlabelled proteins and that these proteins can be directly detected by virtue of the fluorescent moiety. Cells not treated with CysNO show no fluorescently tagged proteins, indicating that this treatment was specific for S-nitrosated proteins.

Mito-btDEPMPO trapped this protein radical to give an EPR signal, indicating that neither the biotin group nor the TPP group interfere with the ability of the cyclic nitrone to trap the protein radical. Mito-btDEPMPO is able to trap to trap the protein radical and the spin adduct is stable enough to be detected by Western blot analysis. The biotin group, however, functions as the detecting moiety; whereas, TPP functions as the targeting moiety, targeting the spin trapping compound to mitochondria.

Example 6

The Data Shown in FIGS. 9 and 10 was Generated in Accordance with the Following Protocol Sample Preparation for Spin-Trapping with Bio-Green DEPMPO.

Co-incubate aliquot of hem protein (500 µM), Bio-Green DMPO (20 mM) with hydrogen peroxide (1 mM) or NaNO2 (1 mM) in 50 mM phosphate buffer (pH 7.4, containing 1 mM DTPA) for one hour at room temperature.

Diluted two-fold with Laemmli sampling buffer, add DTT (10 mM final concentration), and incubated at 80° C. for 10 min.

Samples are subject to gel electrophoresis and fluorescence detection.

Samples.
1. metmyoglobin+Bio-Green DEPMPO
2. metmyoglobin+H2O2+Bio-Green DEPMPO
3. methemoglobin+Bio-Green DEPMPO
4. methemoglobin+H2O2+Bio-Green DEPMPO
5. oxyhemoglobin+Bio-Green DEPMPO
6. oxyhemoglobin+NaNO2+Bio-Green DEPMPO The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A spin trapping compound for analyzing free radicals having:
a nitrone of a structure of:

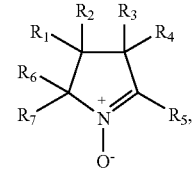

wherein $R_1$, $R_2$, $R_3$, $R_4$, $R_5$, $R_6$ and $R_7$ are independently selected from the group consisting of deuterium, hydrogen, a hydrocarbon, a halogenalkane, an oxygen-containing group, a nitrogen-containing group and a phosphorus- and sulfur-containing group, wherein at least one of $R_1$, $R_2$, $R_3$, $R_4$, $R_5$, $R_6$ and $R_7$ contains nitrogen, phosphorus, or oxygen;
a linker attached at $R_1$, $R_2$, $R_3$, $R_4$, $R_5$, $R_6$ or $R_7$; and
a detecting moiety separate from $R_1$, $R_2$, $R_3$, $R_4$, $R_5$, $R_6$ or $R_7$ that is attached to the linker, wherein the detecting moiety is selected from the group consisting of biotin, a positron emission tomography (PET) radiotracer, a single photon emission computed tomography (SPECT) radiotracer, a radiotracer contrast agent, a chromogenic molecule, a fluorescent molecule, and a radioactive molecule.

2. The spin trapping compound of claim 1, wherein the nitrone is a member selected from the group consisting of 5-(diethoxy-phosphoryl)-5-methyl-1-pyrroline-N-oxide, 5-tert-butoxycarbonyl 5-methyl-1-pyrroline N-oxide, 5-(diisopropoxyphosphoryl)-5-methyl-1-pyrroline-N-oxide, 5-ethoxycarbonyl-5-methyl-1-pyrroline N-oxide, 5-carbamoyl-5-methyl-1-pyrroline N-oxide, 5,5-dimethyl-1-pyrroline 1-oxide, 5-(dipropoxyphosphoryl)-5-methyl-1-pyrroline N-oxide, 5-(di-n-butoxyphosphoryl)-5-methyl-1-pyrroline N-oxide and 5-(bis-(2-ethylhexyloxy)phosphoryl)-5-methyl-1-pyrroline N-oxide.

3. The spin trapping compound of claim 1, wherein the nitrone is 5-(diethoxy-phosphoryl)-5-methyl-1-pyrroline-N-oxide.

4. The spin trapping compound of claim 1, wherein the linker is a member selected from the group consisting of a hydrocarbon, a polyester, a polyethylene glycol, a carbohydrate, a fluorocarbon, a nucleic acid, a peptide, a polyamine and an amino acid.

5. The spin trapping compound of claim 1, wherein the detecting moiety is biotin.

6. The spin trapping compound of claim 1, further having a targeting moiety linked to the linker or linked directly to the nitrone at a R group not occupied by the linker and detecting moiety, wherein the targeting moiety is a member selected from the group consisting of an organ targeting agent, a cell targeting agent, an organelle targeting agent and a molecule targeting agent.

7. The spin trapping compound of claim 6, wherein the organelle targeting agent is a mitochondria targeting agent.

8. The spin trapping compound of claim 7, wherein the mitochondria targeting agent is a member selected from the group consisting of a triphenylphosphonium cation, a pyridinium cation and a tetraalkyl ammonium cation.

9. A method of detecting free radicals comprising:
reacting a free radical with any one of the compounds of claim 1 to form a spin adduct; and
detecting the spin adduct via the detecting moiety.

10. The method of claim 9, wherein the free radical is a protein free radical.

11. The method of claim 10, further comprising photolytically cleaving the protein free radical during the reacting step.

12. The method of claim 9, wherein the detecting moiety is detected by a method selected from the group consisting of enzyme-linked immunosorbent assays, fluorescence microscopy, fluorescence spectroscopy, Northern blot analysis, Southern blot analysis, Western blot analysis, Immunodot assays, high performance liquid chromatography, mass spectrometry, magnetic resonance imaging, positron emission tomography and single photon emission computed tomography.

13. The method of claim 9, further comprising detecting the spin adduct by electron paramagnetic resonance.

* * * * *